(12) United States Patent
Carriço et al.

(10) Patent No.: US 8,800,819 B2
(45) Date of Patent: Aug. 12, 2014

(54) DISCHARGING DEVICE FOR DISPENSING LIQUIDS

(75) Inventors: Silvio Carriço, Singen (DE); Michael Helmlinger, Radolfzell (DE); Joerg Kohnle, Schwenningen (DE)

(73) Assignee: Aptar Radolfzell GmbH, Radolfzell (DE)

(*) Notice: Subject to any disclaimer, the term of this patent is extended or adjusted under 35 U.S.C. 154(b) by 206 days.

(21) Appl. No.: 13/200,682

(22) Filed: Sep. 28, 2011

(65) Prior Publication Data

US 2012/0080448 A1 Apr. 5, 2012

(30) Foreign Application Priority Data

Sep. 30, 2010 (DE) .......................... 10 2010 047 847

(51) Int. Cl.
| | |
|---|---|
| B05B 12/02 | (2006.01) |
| A61M 15/00 | (2006.01) |
| A61M 15/08 | (2006.01) |
| B05B 11/00 | (2006.01) |

(52) U.S. Cl.
CPC ......... *A61M 15/0065* (2013.01); *A61M 15/008* (2013.01); *A61M 15/0081* (2013.01); *A61M 15/08* (2013.01); *B05B 11/3059* (2013.01); *A61M 15/0083* (2013.01); *A61M 2205/3317* (2013.01); *A61M 2205/6054* (2013.01); *A61M 2205/502* (2013.01)
USPC ....... 222/153.13; 222/23; 222/52; 222/321.7; 222/644

(58) Field of Classification Search
USPC .................... 222/23, 153.04, 153.11, 153.13, 222/153.14, 638, 642, 644
See application file for complete search history.

(56) References Cited

U.S. PATENT DOCUMENTS

| 6,454,185 B2 | 9/2002 | Fuchs |
| 7,100,601 B2* | 9/2006 | Bruna ....................... 128/200.14 |
| 8,210,403 B2* | 7/2012 | Malorni et al. ................ 222/648 |

(Continued)

FOREIGN PATENT DOCUMENTS

| DE | 10 2008 064 559 A1 | 4/2010 |
| EP | 1 125 637 A2 | 8/2001 |
| WO | WO 2006/095194 A1 | 9/2006 |

OTHER PUBLICATIONS

Examination Report issued by the German Patent Office for Application No. 10 2010 047 847.4 dated Nov. 16, 2011 (4 pages).

(Continued)

*Primary Examiner* — Daniel R Shearer
(74) *Attorney, Agent, or Firm* — Flynn, Thiel, Boutell & Tanis, P.C.

(57) ABSTRACT

A discharging device for dispensing liquids having a housing, control electronics, a liquid storage receptacle, a discharge orifice, a conveying device actuable manually by a first actuator which transports the liquid to the discharge orifice from the storage receptacle and a blocking device, which in a blocked state blocks the actuation of the conveying device and in a released state allows actuation of the conveying device. The blocking device includes an interlock device movable relative to the housing between first and second positions and a movement of the interlock device from the first to the second position causes the blocking device to assume the released state. The interlock device is biased by a spring device in the direction of the second position and a first retaining device is provided which retains the interlock device in the first position and which is releasable by a signal from the control electronics.

16 Claims, 5 Drawing Sheets

(56) References Cited

U.S. PATENT DOCUMENTS

| | | |
|---|---|---|
| 2001/0015387 A1 | 8/2001 | Fuchs |
| 2002/0000225 A1* | 1/2002 | Schuler et al. ........... 128/200.14 |
| 2004/0069798 A1* | 4/2004 | Grey et al. ...................... 222/52 |
| 2009/0084818 A1* | 4/2009 | Chung et al. ............. 222/153.02 |
| 2010/0084433 A1 | 4/2010 | Cater et al. |

OTHER PUBLICATIONS

European Patent Office Search Report dated Jan. 26, 2012 with English translation of categories of cited documents (5 pages).

* cited by examiner

DISCHARGING DEVICE FOR DISPENSING LIQUIDS

FIELD AND BACKGROUND OF THE INVENTION

The invention relates to a discharging device for dispensing liquids, more particularly for dispensing pharmaceutical liquids, which discharging device includes a housing, control electronics, a liquid storage receptacle for storing the liquid prior to discharge thereof, a discharge orifice, a conveying device which can be operated manually by means of a first actuator and by means of which the liquid can be conveyed from the liquid storage receptacle to the discharge orifice for the purpose of dispensing the same, and a blocking device that can assume a blocked state, in which operation of the conveying device is mechanically blocked, and a released state, in which operation of the conveying device is possible, for the purpose of preventing another discharging operation from taking place during a blocking period following a discharging operation. For this purpose, the blocking device of a generic discharging device includes an interlock device that is capable of being moved relative to the housing between a first and a second position, the blocking device being configured such that a movement of the interlock device from its first position to its second position causes the blocking device to assume the released state. The interlock device is spring biased by a spring device in the direction of its second position. Furthermore, there is provided a first retaining device, by means of which the interlock device can be retained against the force of this spring device in its first position and which can be released by an electrical signal generated by the control electronics.

A generic discharging device is disclosed in DE 10 2008 064 559 A1. Provision is made in this device for the mechanical work involved in moving the blocking device between the blocked state and the released state to be imparted to the system by the user during the actuation of the device for the purpose of carrying out a discharging operation. Following the discharging operation, this mechanical work is stored in one or more spring devices held in the tensioned state by a retaining device. This retaining device is formed by a permanent magnet and an electromagnet in the embodiments disclosed in DE 10 2008 064 559 A1, the permanent magnet performing the actual retaining function, whilst it is rendered temporarily ineffective by means of the electromagnet for the purpose of transferring the blocking device to the released state, which is thus achieved. Thus the retaining device is released by activation of the electromagnet.

The interlock device of a generic discharging device need not directly serve for blocking the conveying device. Thus both the push rod 78 and the bolt 142 described in DE 10 2008 064 559 A1 are interlock devices in terms of the present invention, since the displacement thereof directly or indirectly results in achieving the released state of the blocking device.

The design of the retaining device as a permanent magnet and an electromagnet constitutes a very advantageous solution, but it also involves the problem that strong impacts, caused accidentally or willfully, may cause unwanted movement of the blocking device so as to achieve the released state before the blocking period has elapsed. This poses the risk of administration of an overdose of the active ingredient stored in the liquid storage receptacle.

SUMMARY OF THE INVENTION

It is an object of the invention to improve a generic discharging device to safeguard it from administration of an overdose.

According to the invention, this is achieved by the provision of a second retaining device for this purpose, by means of which the interlock device can be retained in the first position against the force of the spring device and which can be released by manual operation.

Thus, in addition to the first retaining device that can be released by the control electronics, the discharging device of the invention includes a second retaining device, which is operated by the user of the discharging device in accordance with its intended use. For example, a second actuator can be provided on the discharging device for this purpose. Due to the fact that the second retaining device is released manually, it can be configured to be more robust than the first retaining device in such a way that an impact on the discharging device does not result in displacement of the interlock device. More particularly, the second retaining device can hold the interlock device positively in its first position, for example by means of an additional retaining element that impedes the movement of the interlock device from its first position to its second position as long as there is no manual operation of the second retaining device by the user.

In order to move the interlock device to its second position, both retaining devices must be released—the first retaining device by means of the electrical signal and the second retaining device by means of manual control by the user.

Preferably, a discharging device of the invention comprises a first retaining device comprising a permanent magnet that is disposed and configured such that it can hold the interlock device in its first position. This embodiment comprising a permanent magnet has proved to be very advantageous, since the transfer of the interlock device to its first position itself results in establishment of the retained state without requiring the first retaining device to have additional mechanically displaceable components. Likewise, it is regarded as being advantageous when the first retaining device comprises an electromagnet, which, when powered sufficiently by the control electronics, results in the application of force to the interlock device, which applied force overcomes a retention force of the permanent magnet and thus causes the first retaining device to be released.

It is also advantageous when a sensor connected to the control electronics is provided for detecting the release of the second retaining device, the control electronics being configured to release the first retaining device in response to detection of the release of the second retaining device, provided that the blocking period has elapsed.

In this development, the first retaining device is thus not released permanently after the expiry of the blocking period, for example, by permanent application of power to the electromagnet, since this might involve high energy consumption depending on the configuration of the first retaining device. Instead, when the blocking period has expired, the control electronics assume a state in which they also release the first retaining device on detecting the manually triggered release of the second retaining device. The relevant sensor can be mounted on an actuator for the second retaining device or on the aforementioned retaining element provided for the purpose of preventing displacement of the interlock device to its second position.

Since it is not readily apparent to a user as to whether the blocking period has elapsed or not in such an embodiment in which the first retaining device is not released permanently following the expiry of the blocking period, it is regarded as being advantageous when a display device connected to the control electronics is provided, the control electronics being configured to indicate the expiry of the blocking period by way of the display device. The display device can be configured to provide acoustic and/or visual signals. It is preferable to use a liquid crystal display or a comparable display on which an appropriate symbol, for example a padlock, appears and then disappears on expiry of the blocking period. It is very preferable for three different symbols to be provided on the display so as to make it possible to distinguish between the three states of the discharging device, namely "locked, not releasable", "locked, releasable", and "unlocked, ready for use". This can be achieved, for example, by a symbol on the display that turns on, blinks, or turns off depending on the state of the discharging device. Thus the user can recognize the current state of the discharging device by viewing the display. More particularly, any malfunction of the device preventing a changeover between two states can be readily detected.

Preferably, the second retaining device includes a retaining element which is capable of being moved relative to the housing by means of a second actuator and which assumes a retaining position for the purpose of mechanically preventing any movement of the interlock device, and which can be moved from this retaining position by means of the second actuator.

In a particularly simple embodiment, the actuator and the retaining element are in the form of a single component that is mounted on the housing so as to carry out a translatory or pivotal movement. Preferably, the retaining element is biased by a spring in the retaining position so that it automatically re-assumes the retaining position when the second retaining device has been manually released.

In a particularly advantageous embodiment, there is further provided a damping device that retards the movement between the retaining element and the housing. As a result, not even a very severe shock will be able to simultaneously result in a release of the first retaining device and of the second retaining device, since the damping device impedes rapid displacement of the retaining element. Preferably, the damping device can be provided in the form of a resiliently deformable component, for example, a foamed element that is deformed during the movement of the retaining element. The energy required for displacing the retaining element can be easily introduced by means of the second actuator, whereas a temporary shock to the discharging device, for example, when the latter is dropped onto the floor, is not sufficient to cause displacement of the retaining element.

BRIEF DESCRIPTION OF THE DRAWINGS

Additional aspects and advantages of the invention are revealed in the claims and in the following description of a preferred exemplary embodiment of the invention that is explained with reference to the drawings, in which:

DETAILED DESCRIPTION

Figure 1:
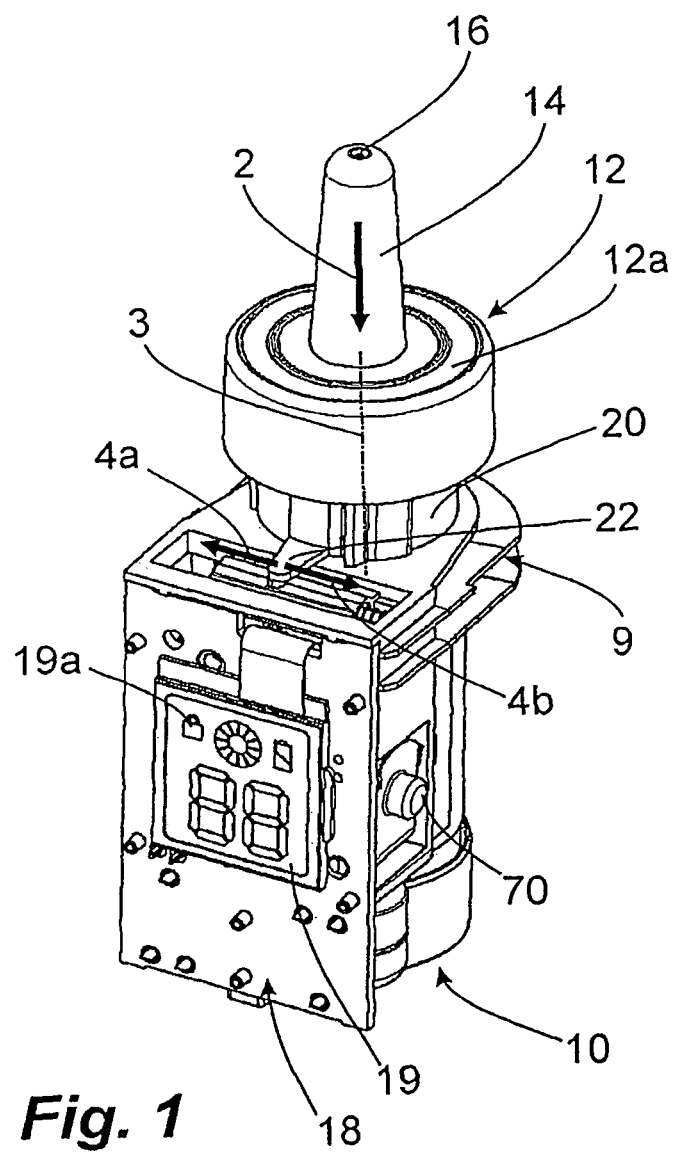
FIG. 1 is an overall view of the discharging device of the invention, in which the external housing is removed, and FIG. 2a to FIG. 5b each constitute two illustrations of an application cycle of the discharging device shown in FIG. 1, starting from a blocked state of the device to the production of the released state to the restoration of the blocked state upon completion of the discharging operation.

FIG. 1 shows a discharging device of the invention, in which an external part of a housing 9 is removed for the purpose of illustrating the construction of the device.

The discharging device has a liquid storage receptacle 10 and an applicator 12 including a nasal tube 14. The applicator 12 is adapted to be depressed relatively to the liquid storage receptacle 10 in the direction of the arrow 2 by means of an actuator 12a, in order to actuate an internal conveying device (not shown) in the form of a piston pump. During the course of such actuation of the conveying device, a pharmaceutical liquid, for example an analgesic, is drawn from the liquid storage receptacle 10 and delivered to a discharge orifice 16 located at the distal end of the nasal tube 14, where it is dispensed in the form of a spray jet.

For the purpose of temporarily preventing a discharging operation, a blocking ring 20 is provided, which is mounted for rotation about an axis 3 oriented in the direction of actuation 2 and which, depending on its angular position, prevents the applicator 12 from being depressed by means of locating surfaces (not shown in the drawing). On the blocking ring 20, a tab 22 is provided pointing outwardly in the radial direction for displacement, as described below in more detail, for the purpose of rotating the blocking ring 20.

The discharging device is closed at the front by control electronics 18 comprising a liquid crystal display 19 for indicating status information.

These control electronics are configured to move the blocking ring 20, at the end of a blocking period during which no discharging operation may take place, in the direction of the arrow 4a by means of the tab 22 into its released position or to initiate this movement of the blocking ring 20. When the blocking ring is in this released position, a discharging operation can be effected by depressing the applicator 12, as mentioned above. When this discharging operation has been carried out, the blocking ring 20 returns automatically in the direction of the arrow 4b, and a new blocking period is started. The released state of the discharging device is restored by the control electronics 18 only after the blocking period has elapsed.

FIGS. 2a to 5b show the components for maintaining the blocked state and illustrate the cooperation thereof. For this purpose, FIGS. 2a to 5b each show, on the one hand, the discharging device in its entirety with the control electronics 18 removed, and a separate illustration of the components of a blocking device 30 of the discharging device, as are essential to the invention, on the other hand.

The essential components are explained below with reference to FIGS. 2a and 2b. The tab 22 located on the blocking ring 20, mentioned above, is guided by a slide 32 which is capable of being moved linearly in the direction of the arrow 6 and which is biased by a spring 34 in the direction 6a in which it must be moved for the purpose of producing the released state of the discharging device. The movement of the slide 32 in the direction 6a is temporarily prevented by means of an interlock device 40 and the retaining extension 40d thereof. This interlock device 40 is hingedly mounted on the housing so as to be pivotal about an axis 7 and is torque-biased by a spring 42 in the counterclockwise direction with reference to the view shown in the drawings. The fact that this torque bias applied by the spring 42 does not immediately cause pivoting of the interlock device 40 in the counterclockwise direction and thus a release of the slide 32 and its displacement in the direction 6a is due to the presence of two retaining devices 50, 60 adapted to prevent the interlock device 40 from pivoting.

The first retaining device 50 is formed by a permanent magnet 52, for which a main section 40a of the interlock device 40 represents a pivotal anchor. Retained by the force of this permanent magnet, the free end 40b of the interlock device 40 therefore bears against a contact surface 54 of the permanent magnet 52 in the blocked state of the blocking device 30, which contact surface 54 is stationary relative to the housing 9. In the neutral state, the magnetic force of the permanent magnet 52 of the first retaining device 50 is alone sufficient to prevent the interlock device 40 from pivoting in the counterclockwise direction from the position shown in FIGS. 2a and 2b.

However, a second retaining device 60 is provided, since the magnetic retention force might be overcome if the discharging device should receive a sharp blow, for example when the discharging device is dropped. This second retaining device 60 comprises a retaining element 62 which can pivot about a pivot axis 8 and comprises a retaining member 64 that likewise prevents the interlock device 40 from pivoting in the counterclockwise direction by means of a contact surface 64a. This retaining element 62 is torque biased by a spring 66 in the clockwise direction and is therefore securely retained in its retaining position shown in FIGS. 2a and 2b. The retaining element 62 is connected for co-rotation to a second actuator or button 70 that is accessible from the outside through a recess of the housing, as shown in FIG. 1. It is possible by means of this actuator 70 to pivot the retaining element 62 and thus also the retaining member 64 and the contact surface 64a against the force of the spring 66 in the counterclockwise direction.

As mentioned above, FIGS. 2a and 2b illustrate the blocked state of the blocking device 30. In this blocked state, the interlock device 40 is held in position against the force of the spring 42 by both the first retaining device 50 and the second retaining device 60 so that it prevents, by means of the retaining extension 40d, any displacement of the slide 32 in the direction 6a and thus any movement of the blocking device 30 to attain the released state.

Figure 3A:
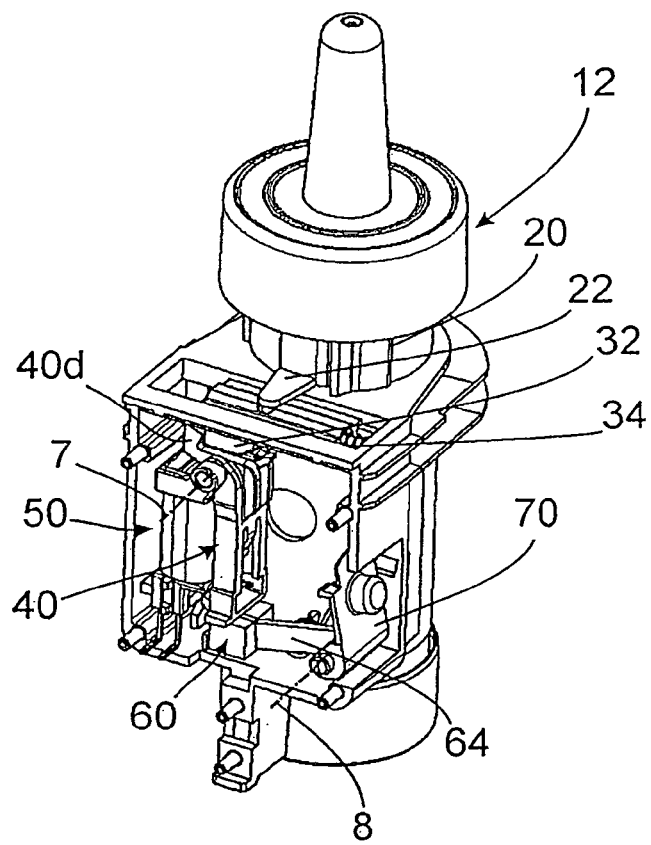
Figure 3B:
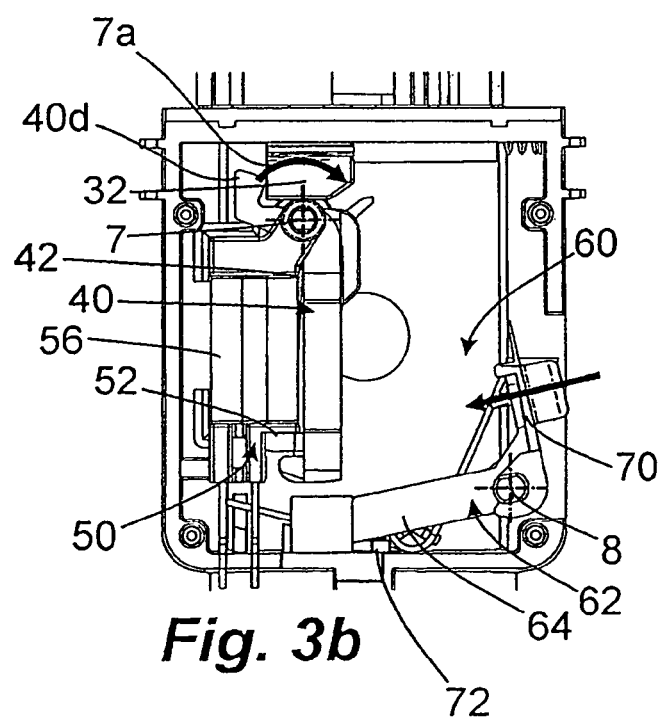

Isolated manual actuation of the actuator 70 in this state does cause pivoting of the retaining member 64 in the counterclockwise direction, as shown in FIGS. 3a and 3b. This only releases the second retaining device 60, while the first retaining device 50 holds the interlock device 40 unchanged in its first position on account of the permanent magnet 52 and thus prevents the discharging device from assuming the released state. However, the actuation of the actuator 70 is detected by means of a sensor 72 and is transmitted to the control electronics 18. During the blocking period, this detection does not cause the control electronics to exert any influence on the first retaining device 50.

As soon as a blocking period, during which no discharging operation is possible in accordance with the designated use of the discharging device, has elapsed, this is indicated on the LC display 19 in that a symbol 19a previously displayed in a steady form assumes a blinking state. The user thus learns that the discharging device has entered a still locked but releasable state from a locked and non-releasable state. When the retaining element 62 comprising the retaining member 64 is pivoted by means of the actuator 70 following the thus indicated termination of the blocking period, as shown in FIGS. 3a and 3b, this is detected by the sensor 72, and the first retaining device 50 is released by the control electronics 18 in addition to the second retaining device due to the fact that the blocking period has elapsed. An electromagnet 56 is energized for this purpose. This electromagnet 56 compensates for the retention force of the permanent magnet 52 so that as a result the torque of the spring 42 suffices to pivot the interlock device 40 about the axis 7 in the direction of the arrow 7a.

Figure 4A:
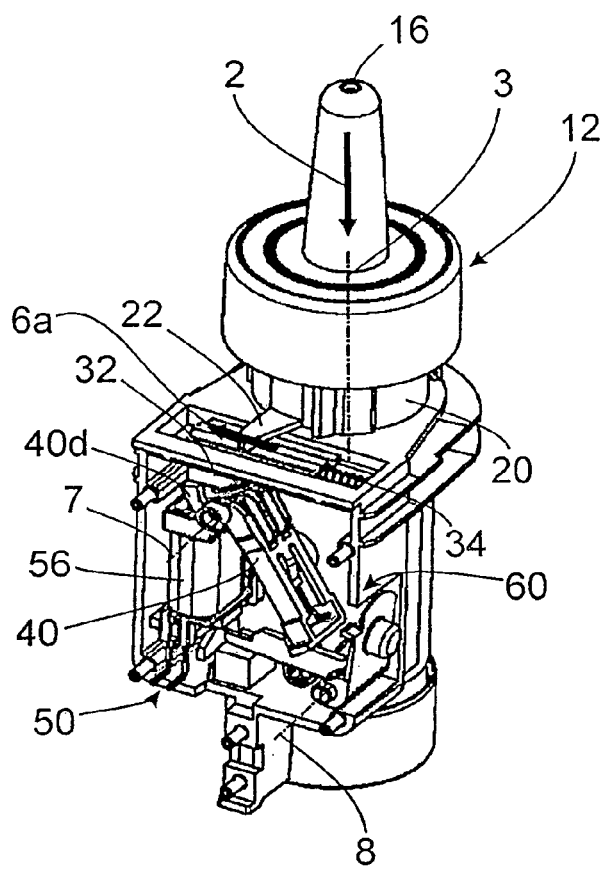
Figure 4B:
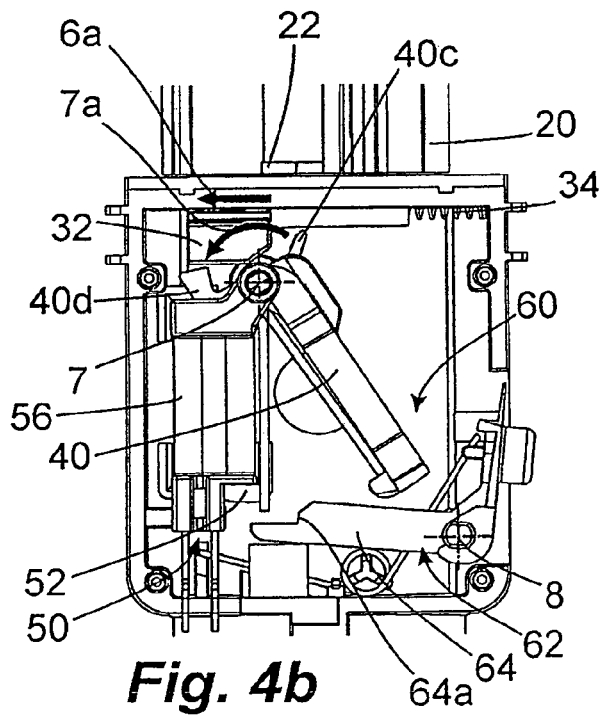

FIGS. 4a and 4b illustrate this pivoting of the interlock device 40 together with the retaining extension 40d. As a result of such pivoting, the slide 32 driven by the spring 34 is displaced in the direction of the arrow 6a, and thus the blocking ring 20 is pivoted about the axis 3 in such a way that it no longer prevents the applicator 12 from being depressed. An unlocked state of the discharging device is thus established. This unlocked state is represented on the display 19 in that the symbol 19a no longer blinks, but is instead displayed in a steady state. As long as the discharging device is in the unlocked state shown in FIGS. 4a and 4b, it is thus possible for the user to actuate the conveying device (not shown) by depressing the applicator 12 and thus dispensing the pharmaceutical liquid through the discharge orifice 16.

When the applicator 12 is depressed during this discharging operation and/or during the subsequent return stroke of the applicator 12, the slide 32 is moved back in the direction of the arrow 6b by a sliding block guide (not shown), as disclosed in DE 10 2008 064 559 A1, with the slide causing pivoting of the interlock device 40, by means of a return section 40c of the interlock device 40 counteracting the force of the spring 42, about the axis 7 in the direction of the arrow 7b. In this way, the interlock device 40 travels back to its position shown in FIGS. 2 and 3, as is evident from FIGS. 5a and 5b. The first retaining device 50 comprising the permanent magnet 52 holds the interlock device 40 in the first position thus achieved, in the same manner as the retaining member 64, which is deflected temporarily against the force of the spring 66 when the interlock device attains the first position shown in FIGS. 5a and 5b from its second position shown in FIGS. 4a and 4b to subsequently come to again bear against the interlock device 40 by way of the contact surface 64a.

Thus the blocked state is again achieved and another blocking period commences, at the end of which the released state can be restored by the user in the manner described. This is represented on the display 19 during the blocked state by the symbol 19a being shown in an uninterrupted form.

The discharging device illustrated very effectively assures the maintenance of the blocked state, during which no discharging operation is possible. The use of two retaining devices 50, 60 greatly reduces the risk of this blocked state being overridden by a single shock to the discharging device and before the blocking period has elapsed. Such a shock may indeed temporarily exceed the retention force of the permanent magnet 52, but in the case of such a shock, the retaining device 60 is not released due to its spring bias so that the two retaining devices 50, 60 re-establish the blocked state once the shock has expired. In order to ensure that the second retaining device 60 is insensitive to shock, a foamed rubber block 80 is provided in the embodiment shown to act as a brake and thus allow the retaining element 62 to be deflected during manual actuation of the actuator 70 but to prevent deflection of the retaining element 62 on the occurrence of a temporary shock.

Figure 2A:
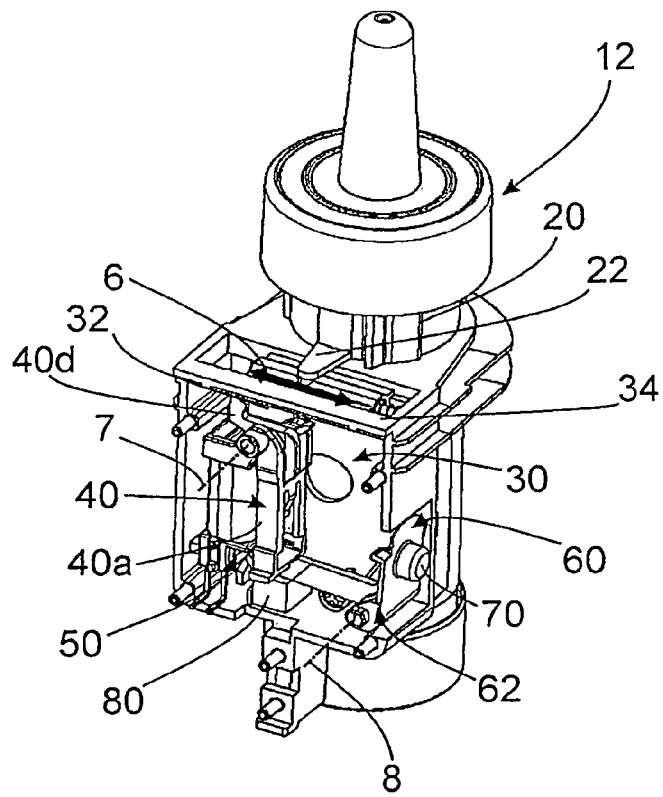
Figure 2B:
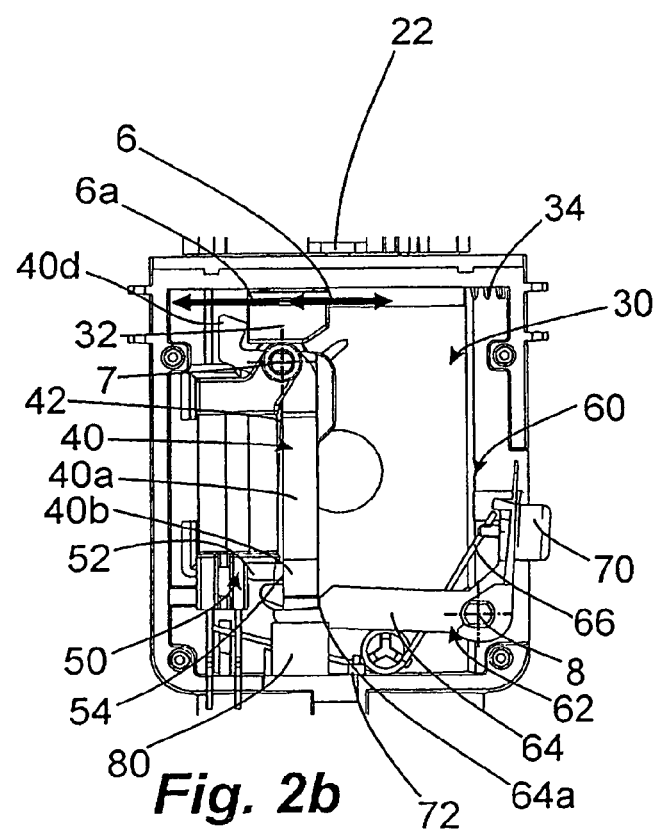
Figure 5A:
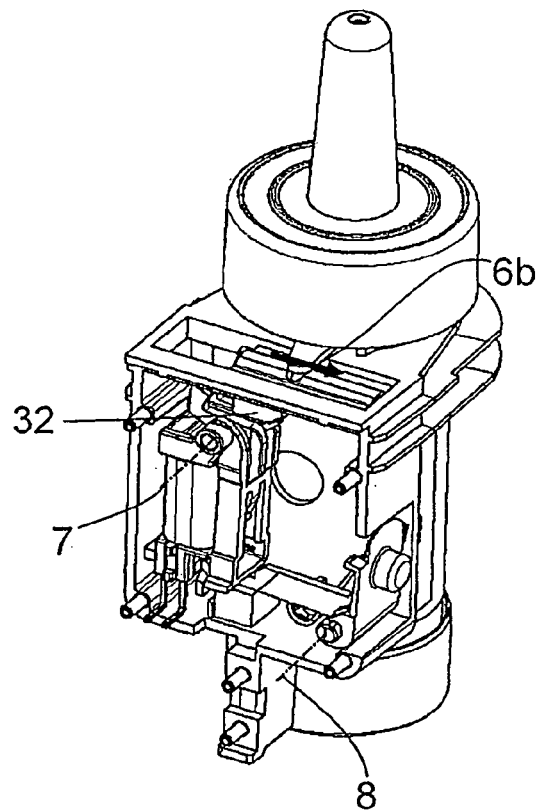
Figure 5B:
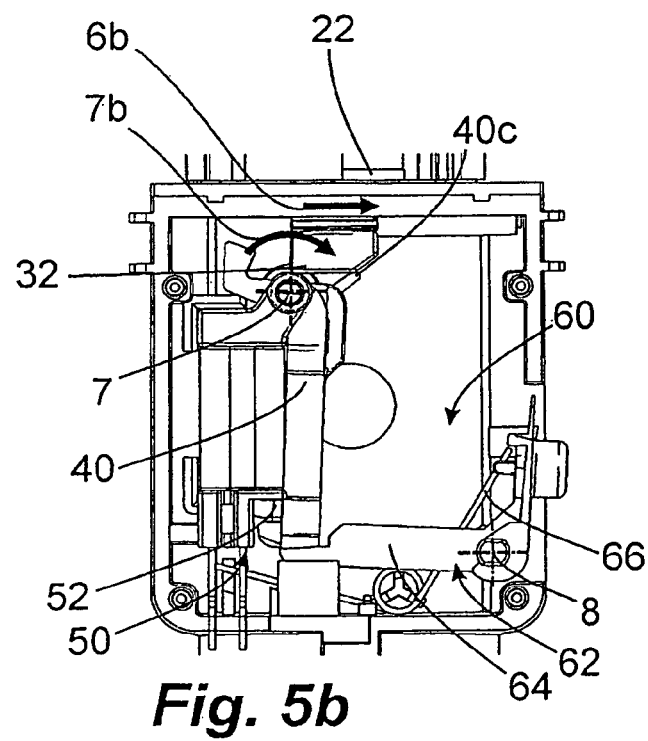

As shown in FIGS. 5a and 5b, the slide 32 is displaced in the direction of the arrow 6b far beyond its position in the blocked state of the blocking device 30, as shown in FIGS. 2a and 2b, during its movement in the direction of the arrow 6b, this relating to the design of the sliding block guide described above and explained in DE 10 2008 064 559 A1. There can be provided an additional damper or brake, for example on the slide 32 itself or also on the bearing of the interlock device 40, in order, when the actuator 70 is depressed permanently, to prevent the retention force of the first retaining device 50 from being immediately overcome as a result of the reverse movement of the slide 32 in the direction of the arrow 6a following the state shown in FIGS. 5a and 5b.

The invention claimed is:
1. A discharging device for dispensing a pharmaceutical liquid, comprising:
 a housing,
 control electronics, a liquid storage receptacle for storing the pharmaceutical liquid prior to discharge thereof, a discharge orifice, a conveying device actuatable manually by a manual actuator which causes transport of the pharmaceutical liquid to said discharge orifice from said storage receptacle for the purpose of dispensing the pharmaceutical liquid, and a blocking device, having a blocked state in which the actuation of said conveying device is mechanically blocked in order to prevent another discharge from taking place during a blocking period following a discharging operation, and a released state in which the actuation of said conveying device is possible, wherein the blocking device comprises an interlock device movable relative to the housing between a first and a second position, said blocking device being configured such that a movement of said interlock device from the first position to the second position causes said blocking device to assume the released state, and wherein the interlock device is spring biased by a spring device in the direction of the second position, a first retaining device is provided which retains said interlock device in the first position against the force of said spring device and which is released by an electrical signal generated by said control electronics, a second retaining device is provided which retains said interlock device in the first position against the force of said spring device and which is released by manual actuation, the interlock device moving into the second position only when both the first and second retaining devices are released, the first retaining device being released by the control electronics and the second retaining device being released by manual actuation by the user, a sensor connected to said control electronics is provided for detection of the release of said second retaining device, the control electronics being adapted to react to the sensed release of said second retaining device by releasing said first retaining device, provided that the blocking period has elapsed.

2. The discharging device as defined in claim 1, wherein said first retaining device comprises a permanent magnet disposed and configured to retain said interlock device in the first position.

3. The discharging device as defined in claim 2, wherein said first retaining device comprises an electromagnet which when sufficiently energized applies force to said interlock device which overcomes the retaining force of said permanent magnet so as to release said first retaining device.

4. The discharging device as defined in claim 1, wherein a display device connected to said control electronics is provided, the control electronics being adapted to indicate the expiry of the blocking period by means of the display device.

5. The discharging device as defined in claim 1, wherein the manual actuator is a first manual actuator and said second retaining device comprises a retaining element movable relative to said housing by a second manual actuator, the retaining element in a retaining position mechanically preventing any movement of said blocking element and being movable out of the retaining position by said second manual actuator.

6. The discharging device as defined in claim 5, wherein a damping device which retards the movement between the retaining element and the housing is provided, said damping device being in the form of a foamed block which is compressed when the retaining element is displaced.

7. The discharging device as defined in claim 1, wherein the interlock device is mounted for pivoting movement relative to the housing between the first and second positions.

8. The discharging device as defined in claim 7, wherein the second retaining device is mounted for pivoting movement relative to the housing.

9. A discharging device for dispensing a pharmaceutical liquid, said discharging device comprising:

a housing;

control electronics disposed on said housing;

a receptacle for storing the pharmaceutical liquid prior to discharge thereof;

a discharge orifice;

a first manual actuator disposed on said housing which when manually actuated causes transport of the pharmaceutical liquid from the receptacle to the discharge orifice to dispense the pharmaceutical liquid;

a blocking device having a blocked state in which actuation of said first manual actuator is mechanically blocked in order to prevent a further discharge of the pharmaceutical liquid during a predefined blocking period occurring after a discharging operation, and a released state in which actuation of said first manual actuator is allowed, said blocking device comprising:

an interlock device pivotably movable relative to said housing between first and second positions wherein movement of said interlock device from the first position to the second position places said blocking device in the released state, said interlock device being biased in the second position by a biasing device;

a first retaining device disposed to retain said interlock device in the first position against the force of said biasing device and being releasable by an electrical signal generated by said control electronics; and a second retaining device disposed to retain said interlock device in the first position against the force of said biasing device, said second retaining device including a second manual actuator having a portion disposed for manual manipulation by a user, wherein said interlock device is movable into the second position only upon release of both said first retaining device by the electrical signal generated by said control electronics and said second retaining device by manual actuation of said portion of said second retaining device by the user;

wherein said discharging device further comprises a sensor disposed to detect the release of said second retaining device, said sensor communicating the release of said second retaining device to said control electronics to cause said control electronics to release said first retaining device after the predefined blocking period has elapsed.

10. The discharging device of claim 9, wherein said second retaining device is pivotably movable relative to said housing between a first blocking position wherein said second retaining device is engaged with said interlock device to retain same in the first position and a second unblocking position wherein said second retaining device is out of engagement with said interlock device.

11. The discharging device of claim 9, wherein said interlock device has a first end disposed to operatively engage said first manual actuator in the first position of said interlock device and a second end disposed to engage said second retaining device in the first position of said interlock device, wherein said interlock device is operatively disengaged from said first manual actuator and is disengaged from said second retaining device when in the second position.

12. The discharging device of claim 10, wherein said portion of said second retaining device is a button actuator disposed externally of said housing and said second retaining device further includes a retaining element connected to said button actuator and disposed internally within said housing, said retaining element engaging said interlock device in the first position.

13. The discharging device of claim 12, wherein said retaining element is non-rotatably connected to said button actuator for pivoting movement therewith, said button actuator and said retaining element when manually actuated by the user pivoting from the first blocking position to the second unblocking position to move said retaining element out of engagement with said interlock device.

14. A discharging device for dispensing a pharmaceutical liquid, said discharging device comprising:
a housing;
control electronics;
a liquid storage receptacle for storing the pharmaceutical liquid prior to discharge thereof;
a discharge orifice;
a conveying device actuable manually by a manual actuator which causes transport of the pharmaceutical liquid to the discharge orifice from the storage receptacle for the purpose of dispensing the pharmaceutical liquid; and
a blocking device having a blocked state in which the actuation of the conveying device is mechanically blocked in order to prevent another discharge from taking place during a blocking period following a discharging operation, and a released state in which the actuation of the conveying device is possible, the blocking device comprising:
an interlock device movable relative to the housing between a first and a second position, the blocking device being configured such that a movement of the interlock device from the first position to the second position causes the blocking device to assume the released state, the interlock device being biased by a spring device in the direction of the second position;
a first retaining device which retains the interlock device in the first position against the force of the spring device and which is released by an electrical signal generated by the control electronics;
a second retaining device which retains the interlock device in the first position against the force of the spring device and which is released by manual actuation; and
a sensor connected to the control electronics for detection of the release of the second retaining device, the control electronics being adapted to react to the sensed release of the second retaining device by releasing the first retaining device provided that the blocking period has elapsed.

15. A discharging device for dispensing a pharmaceutical liquid, comprising:
a housing,
control electronics,
a liquid storage receptacle for storing the pharmaceutical liquid prior to discharge thereof,
a discharge orifice,
a conveying device actuatable manually by a first manual actuator which causes transport of the pharmaceutical liquid to said discharge orifice from said storage receptacle for the purpose of dispensing the pharmaceutical liquid, and
a blocking device, having a blocked state in which the actuation of said conveying device is mechanically blocked in order to prevent another discharge from taking place during a blocking period following a discharging operation, and a released state in which the actuation of said conveying device is possible,
wherein
the blocking device comprises an interlock device movable relative to the housing between a first and a second position, said blocking device being configured such that a movement of said interlock device from the first position to the second position causes said blocking device to assume the released state, and
wherein
the interlock device is spring biased by a spring device in the direction of the second position,
a first retaining device is provided which retains said interlock device in the first position against the force of said spring device and which is released by an electrical signal generated by said control electronics,
a second retaining device is provided which retains said interlock device in the first position against the force of said spring device and which is released by manual actuation, the interlock device moving into the second position only when both the first and second retaining devices are released, the first retaining device being released by the control electronics and the second retaining device being released by manual actuation by the user of a second manual actuator, said second retaining device comprising a retaining element movable relative to said housing by the second manual actuator, the retaining element in a retaining position mechanically preventing any movement of said blocking element and being movable out of the retaining position by said second manual actuator;
wherein
a damping device which retards the movement between the retaining element and the housing is provided, said damping device being in the form of a foamed block which is compressed when the retaining element is displaced.

16. The discharging device as defined in claim 15, wherein the second retaining device is mounted for pivoting movement relative to the housing.

* * * * *